United States Patent
Kraft et al.

(10) Patent No.: US 10,466,957 B2
(45) Date of Patent: *Nov. 5, 2019

(54) ACTIVE ACOUSTIC FILTER WITH AUTOMATIC SELECTION OF FILTER PARAMETERS BASED ON AMBIENT SOUND

(71) Applicant: Dolby Laboratories Licensing Corporation, San Francisco, CA (US)

(72) Inventors: Noah Kraft, Brooklyn, NY (US); Richard Fritz Lanman, III, San Francisco, CA (US); Daniel C. Wiggins, Montecito, CA (US); Jeffrey Baker, Newbury Park, CA (US)

(73) Assignee: Dolby Laboratories Licensing Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,408

(22) Filed: Dec. 16, 2016

(65) Prior Publication Data
US 2017/0099538 A1    Apr. 6, 2017

Related U.S. Application Data

(63) Continuation of application No. 14/819,298, filed on Aug. 5, 2015, now Pat. No. 9,557,960, which is a (Continued)

(51) Int. Cl.
*A61F 11/06* (2006.01)
*G06F 3/16* (2006.01)
(Continued)

(52) U.S. Cl.
CPC .......... *G06F 3/165* (2013.01); *H04R 1/1016* (2013.01); *H04R 1/1083* (2013.01);
(Continued)

(58) Field of Classification Search
CPC ...... H04R 25/00; H04R 25/40; H04R 25/402; H04R 25/405; H04R 25/407; H04R 25/43;
(Continued)

(56) References Cited

U.S. PATENT DOCUMENTS

2001/0005420 A1 *  6/2001  Takagi ................ H04R 25/70
                                                        381/312
2008/0112569 A1     5/2008  Asada
(Continued)

FOREIGN PATENT DOCUMENTS

WO    WO-2012159946 A1 *  11/2012  ............... H03G 3/32

*Primary Examiner* — Leshui Zhang

(57) ABSTRACT

Active acoustic filter systems and methods are disclosed. An active acoustic filter system includes a memory storing one or more stored sound profiles and a respective set of processing parameters associated with each of the one or more stored sound profiles. A processor coupled to the memory generates processed sound by processing ambient sound in accordance with a set of processing parameters retrieved from the memory based on results from comparing an ambient sound profile to at least one of the one or more stored sound profiles.

20 Claims, 9 Drawing Sheets

Related U.S. Application Data continuation-in-part of application No. 14/681,843, filed on Apr. 8, 2015, now Pat. No. 9,524,731.

(60) Provisional application No. 61/976,794, filed on Apr. 8, 2014.

(51) Int. Cl.
| | |
|---|---|
| *H04W 4/50* | (2018.01) |
| *H04R 1/10* | (2006.01) |
| *H04W 4/04* | (2009.01) |
| *A61F 11/14* | (2006.01) |

(52) U.S. Cl.
CPC .......... *H04R 1/1091* (2013.01); *H04W 4/043* (2013.01); *H04W 4/50* (2018.02); *A61F 2011/145* (2013.01); *H04R 2430/01* (2013.01); *H04R 2460/01* (2013.01)

(58) Field of Classification Search
CPC .... H04R 25/50; H04R 25/502; H04R 25/505; H04R 25/507; H04R 25/55; H04R 25/552; H04R 25/554; H04R 25/556; H04R 25/558; H04R 25/35; H04R 25/353; H04R 25/356; H04R 25/45; H04R 25/453; H04R 25/456; H04R 25/04; H04R 25/60; H04R 25/65; H04R 25/652; H04R 25/654; H04R 25/656; H04R 25/658; H04R 25/604; H04R 25/606; H04R 25/608; H04R 2460/01; H04R 2460/17; H04R 2460/13; H04R 1/1016; H04R 1/1008; H04R 1/105; H04R 1/1083; H04R 1/1091; H04R 2430/01; G02C 11/06; G02C 5/143; G06F 17/30749; G06F 17/30761; G06F 13/385; H04M 1/72527; H04M 1/72558
USPC .. 381/72, 73.1, 74, 92, 26, 61, 63, 66, 71.4, 381/71.6, 71.8, 71.9, 71.11, 71.12, 98, 99, 381/100, 101, 102, 103, 312–331, 23.1, 381/60; 455/414.1, 414.2, 404.2, 404.1, 455/440, 422.1, 456.1, 456.2, 456.3, 455/456.4, 456.6, 457; 700/94
See application file for complete search history.

(56) References Cited

U.S. PATENT DOCUMENTS

| | | | | |
|---|---|---|---|---|
| 2008/0187148 | A1* | 8/2008 | Itabashi | G10K 11/178 381/71.6 |
| 2010/0128907 | A1 | 5/2010 | Dijkstra | |
| 2011/0158420 | A1* | 6/2011 | Hannah | H04R 1/105 381/71.6 |
| 2011/0166856 | A1* | 7/2011 | Lindahl | G10L 15/20 704/233 |
| 2011/0293123 | A1* | 12/2011 | Neumeyer | H04R 25/50 381/314 |
| 2014/0079243 | A1* | 3/2014 | Appell | H03G 3/32 381/86 |
| 2014/0277650 | A1* | 9/2014 | Zurek | H04R 3/00 700/94 |

* cited by examiner

ACTIVE ACOUSTIC FILTER WITH AUTOMATIC SELECTION OF FILTER PARAMETERS BASED ON AMBIENT SOUND

CROSS REFERENCE TO OTHER APPLICATIONS

This application is a continuation of U.S. patent application Ser. No. 14/819,298, entitled ACTIVE ACOUSTIC FILTER WITH AUTOMATIC SELECTION OF FILTER PARAMETERS BASED ON AMBIENT SOUND, filed Aug. 5, 2015, which is a continuation in part of U.S. patent application Ser. No. 14/681,843, now U.S. Pat. No. 9,524,731, entitled ACTIVE ACOUSTIC FILTER WITH LOCATION-BASED FILTER CHARACTERISTICS, filed Apr. 8, 2015, which claims priority to U.S. Provisional Application No. 61/976,794, entitled DIGITAL ACOUSTICAL FILTERS FOR USE IN HUMAN EARS AND METHOD FOR USING SAME, filed Apr. 8, 2014, all of which are incorporated by reference for all purposes.

RELATED APPLICATION INFORMATION

This patent is a continuation-in-part of patent application Ser. No. 14/681,843, entitled "Active Acoustic Filter with Location-Based Filter Characteristics," filed Apr. 8, 2015, which claims priority from provisional patent application 61/976,794, entitled "Digital Acoustical Filters for Use in Human Ears and Method for Using Same", filed Apr. 8, 2014, both of which are incorporated herein by reference.

NOTICE OF COPYRIGHTS AND TRADE DRESS

A portion of the disclosure of this patent document contains material which is subject to copyright protection. This patent document may show and/or describe matter which is or may become trade dress of the owner. The copyright and trade dress owner has no objection to the facsimile reproduction by anyone of the patent disclosure as it appears in the Patent and Trademark Office patent files or records, but otherwise reserves all copyright and trade dress rights whatsoever.

BACKGROUND

Field

This disclosure relates generally to digital active audio filters for use in a listener's ear to modify ambient sound to suit the listening preferences of the listener. In particular, this disclosure relates to active audio filters that adapt to the characteristics of the ambient sound.

Description of the Related Art

Humans' perception to sound varies with both frequency and sound pressure level (SPL). For example, humans do not perceive low and high frequency sounds as well as they perceive midrange frequencies sounds (e.g., 500 Hz to 6,000 Hz). Further, human hearing is more responsive to sound at high frequencies compared to low frequencies.

There are many situations where a listener may desire attenuation of ambient sound at certain frequencies, while allowing ambient sound at other frequencies to reach their ears. For example, at a concert, concert goers might want to enjoy the music, but also be protected from high levels of mid-range sound frequencies that cause damage to a person's hearing. On an airplane, passengers might wish to block out the roar of the engine, but not conversation. At a sports event, fans might desire to hear the action of the game, but receive protection from the roar of the crowd. These are just a few common examples where people wish to hear some, but not all, of the sound frequencies in their environment.

In addition to receiving protection from unpleasant or dangerously loud sound levels, listeners may wish to augment the ambient sound by amplification of certain frequencies, combining ambient sound with a secondary audio feed, equalization (modifying ambient sound by adjusting the relative loudness of various frequencies), noise reduction, echo cancellation, or addition of echo or reverberation. For example, at a concert, audience members may wish to attenuate certain frequencies of the music, but amplify other frequencies (e.g., the bass). People listening to music at home may wish to have a more "concert-like" experience by adding reverberation to the ambient sound. At a sports event, fans may wish to attenuate ambient crowd noise, but also receive an audio feed of a sportscaster reporting on the event. Similarly, people at a mall may wish to attenuate the ambient noise, yet receive an audio feed of advertisements targeted to their location. These are just a few examples of peoples' audio enhancement preferences. Further, a person's audio enhancement preferences are individual and change regularly depending on the environment and ambient sound.

Throughout this description, elements appearing in figures are assigned three-digit reference designators, where the most significant digit is the figure number where the element is introduced and the two least significant digits are specific to the element. An element not described in conjunction with a figure has the same characteristics and function as a previously-described element having the same reference designator.

DETAILED DESCRIPTION

Description of Apparatus

Figure 1:
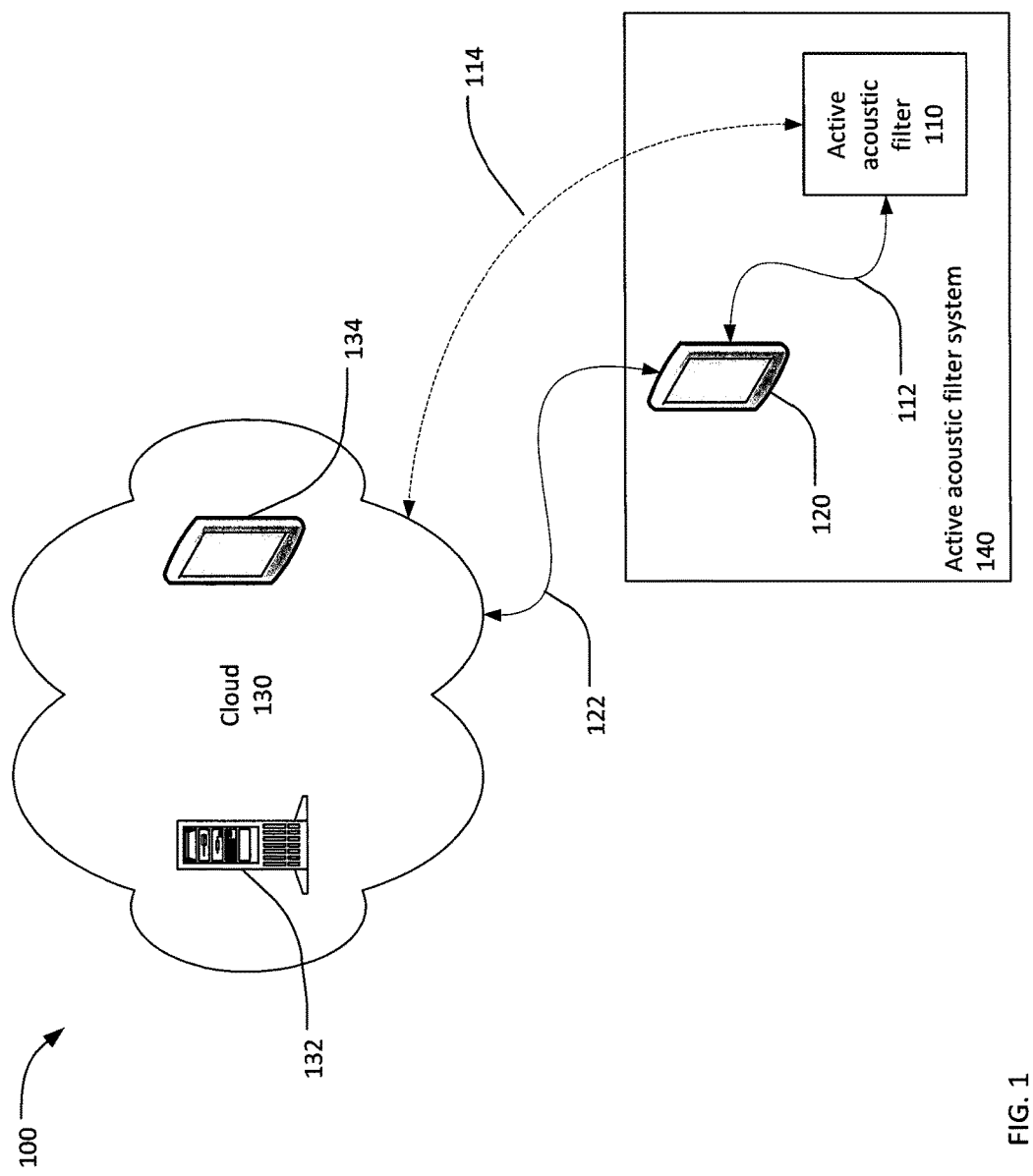
FIG. 1 is a block diagram of an environment.

Referring now to FIG. 1, an environment 100 may include a cloud 130 and an active acoustic filter system 140. In this context, the term "cloud" means a network and all devices that may be accessed by the active acoustic filter system 140 via the network. The cloud 130 may be a local area network, wide area network, a virtual network, or some other form of network together with all devices connected to the network. The cloud 130 may be or include the Internet. The devices within the cloud 130 may include one or more servers 132 and one or more personal computing devices 134.

The active acoustic filter system 140 includes an active acoustic filter 110 and a personal computing device 120.

While the personal computing device 120 is shown in FIG. 1 as a smart phone, the personal computing device 120 may be a smart phone, a desktop computer, a mobile computer, a tablet computer, or any other computing device that is capable of performing the processes described herein. The personal computing device 120 may include one or more processors and memory configured to execute stored software instructions to perform the processes described herein. For example, the personal computing device 120 may run an application program or "app" to perform the functions described herein. The personal computing device 120 may include a user interface comprising a display and at least one input device such as a touch screen, microphone, keyboard, and/or mouse. The personal computing device 120 may be configured to perform geo-location, which is to say to determine its own location. Geo-location may be performed, for example, using a Global Positioning System (GPS) receiver or by some other method.

The active acoustic filter 110 may communicate with the personal computing device 120 via a first wireless communications link 112. The first wireless communications link 112 may use a limited-range wireless communications protocol such as Bluetooth®, Wi-Fi®, ZigBee®, or some other wireless Personal Area Network (PAN) protocol. The personal computing device 120 may communicate with the cloud 130 via a second communications link 122. The second communications link 122 may be a wired connection or may be a wireless communications link using, for example, the WiFi® wireless communications protocol, a mobile telephone data protocol, or another wireless communications protocol.

Optionally, the active acoustic filter 110 may communicate directly with the cloud 130 via a third wireless communications link 114. The third wireless communications link 114 may be an alternative to, or in addition to, the first wireless communications link 112. The third wireless connection 114 may use, for example, the WiFi® wireless communications protocol, or another wireless communications protocol.

Figure 2:
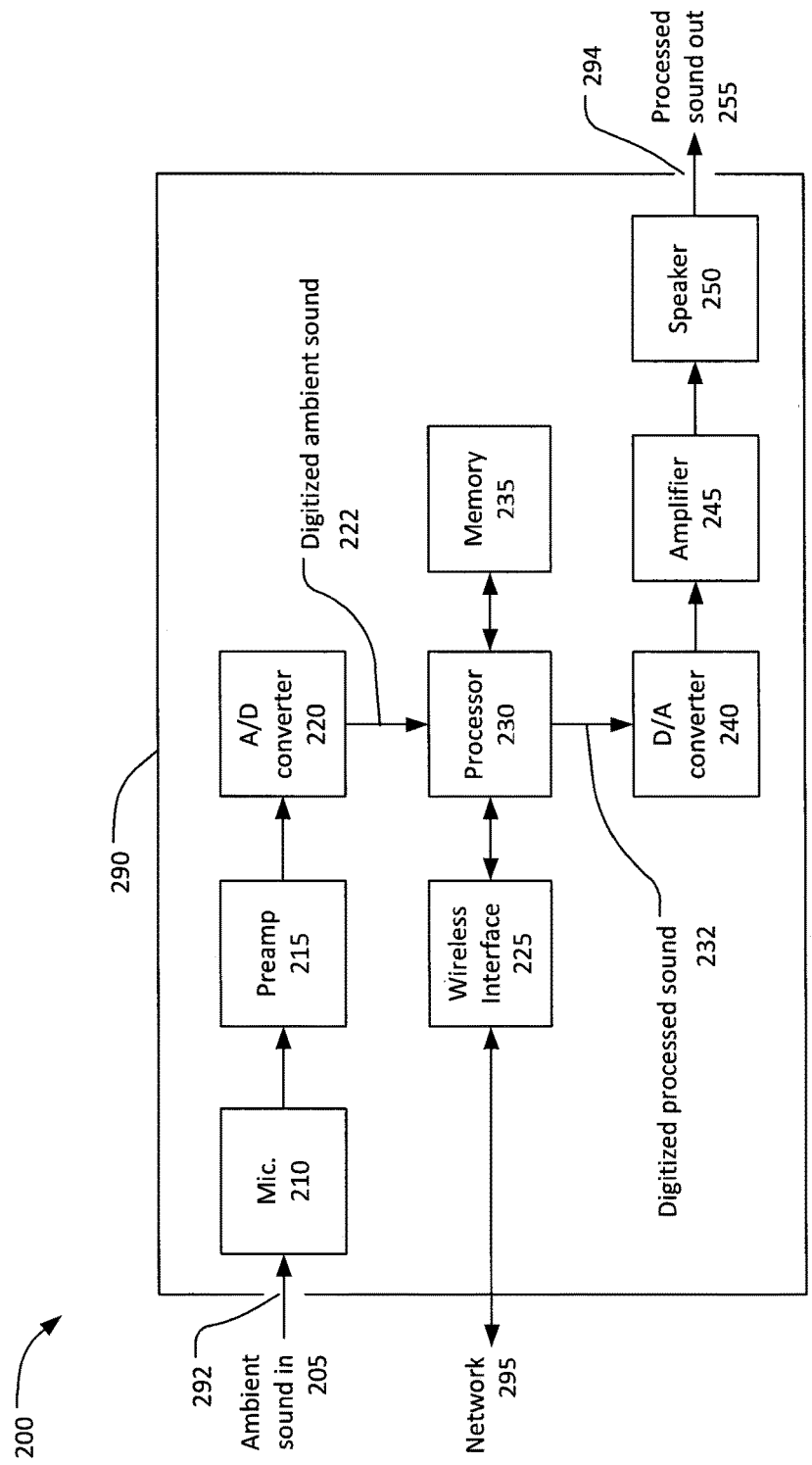
FIG. 2 is block diagram of an active acoustic filter.

FIG. 2 is block diagram of an active acoustic filter 200. The active acoustic filter 200 may include a microphone 210, a preamplifier 215, an analog-to-digital (A/D) converter 220, a wireless interface 225, a processor 230, a memory 235, an analog signal by digital-to-analog (D/A) converter 240, and amplifier 245, a speaker 250, and a battery (not shown), all of which may be contained within a housing 290. The housing 290 may be configured to interface with a user's ear by fitting in, on, or over the user's ear such that ambient sound is mostly excluded from reaching the user's ear canal and processed sound generated by the active acoustic filter is coupled into the user's ear canal. The housing 290 may have a first aperture 292 for accepting ambient sound and a second aperture 294 to allow processed sound to be output into the user's outer ear canal.

The housing 290 may be, for example, an earbud housing. The term "earbud" means an apparatus configured to fit, at least partially, within and be supported by a user's ear. An earbud housing typically has a portion that fits within or against the user's outer ear canal. An earbud housing may have other portions that fit within the concha or pinna of the user's ear.

The microphone 210 converts ambient sound 205 into an electrical signal that is amplified by preamplifier 215 and converted into digital ambient sound 222 by A/D converter 220. The digital ambient sound 222 may be processed by processor 230 to provide digitized processed sound 232. The processing performed by the processor 230 will be discussed in more detail subsequently. The digitized processed sound 232 is converted into an analog signal by D/A converter 240. The analog signal output from D/A converter 240 is amplified by amplifier 245 and converted into processed output sound 255 by speaker 250.

The depiction in FIG. 2 of the active acoustic filter 200 as a set of functional blocks or elements does not imply any corresponding physical separation or demarcation. All or portions of one or more functional elements may be located within a common circuit device or module. Any of the functional elements may be divided between two or more circuit devices or modules. For example, all or portions of the analog-to-digital (A/D) converter 220, the wireless interface 225, the processor 230, the memory 235, the analog signal by digital-to-analog (D/A) converter 240, and the amplifier 245 may be contained within a common signal processor circuit device.

The microphone 210 may be one or more transducers for converting sound into an electrical signal that is sufficiently compact for use within the housing 290.

The preamplifier 215 may be configured to amplify the electrical signal output from the microphone 210 to a level compatible with the input of the A/D converter 220. The preamplifier 215 may be integrated into the A/D converter 220, which, in turn, may be integrated with the processor 230. In the situation where the active acoustic filter 200 contains more than one microphone, a separate preamplifier may be provided for each microphone.

The A/D converter 220 may digitize the output from preamplifier 215, which is to say convert the output from preamplifier 215 into a series of digital ambient sound samples at a rate at least twice the highest frequency present in the ambient sound. For example, the A/D converter may output digital ambient sound 222 in the form of sequential sound samples at rate of 40 kHz or higher. The resolution of the digitized ambient sound 222 (i.e. the number of bits in each sound sample) may be sufficient to minimize or avoid audible sampling noise in the processed output sound 255. For example, the A/D converter 220 may output digitized ambient sound 222 having 12 bits, 14, bits, or even higher resolution. In the situation where the active acoustic filter 200 contains more than one microphone with respective preamplifiers, the outputs from the preamplifiers may be digitized separately, or the outputs of some or all of the preamplifiers may be combined prior to digitization.

The wireless interface 225 may provide digital acoustic filter 200 with a connection to one or more wireless networks 295 using a limited-range wireless communications protocol such as Bluetooth®, Wi-Fi®, ZigBee®, or other wireless personal area network protocol. The wireless interface 225 may be used to receive data such as parameters for use by the processor 230 in processing the digital ambient sound 222 to produce the digitized processed sound 232. The wireless interface 225 may be used to export the digitized processed sound 232, which is to say transmit the digitized processed sound 232 to a device external to the active acoustic filter 200. The external device may then, for example, store and/or publish the digitized processed sound, for example via social media.

The processor 230 may include one or more processor devices such as a microcontroller, a microprocessor, and/or a digital signal processor. The processor 230 can include and/or be coupled to the memory 235. The memory 235 may store software programs, which may include an operating system, for execution by the processor 230. The memory 235 may also store data for use by the processor 230. The data stored in the memory 235 may include, for example, digital sound samples and intermediate results of processes performed on the digital ambient sound 222. The data stored in the memory 235 may also include a user's listening preferences, and/or rules and parameters for applying particular processes to convert the digital ambient sound 222 into the digitized processed sound 232. The memory 235 may include a combination of read-only memory, flash memory, and static or dynamic random access memory.

The D/A converter 240 may convert the digitized processed sound 232 from the processor 230 into an analog signal. The processor 230 may output the digitized processed sound 232 as a series of samples typically, but not necessarily, at the same rate as the digital ambient sound 222 is generated by the A/D converter 220. The analog signal output from the D/A converter 240 may be amplified by the amplifier 245 and converted into processed output sound 255 by the speaker 250. The amplifier 245 may be integrated into the D/A converter 240, which, in turn, may be integrated with the processor 230. The speaker 250 can be any transducer for converting an electrical signal into sound that is suitably sized for use within the housing 290.

The battery (not shown) may provide power to various elements of the active acoustic filter 200. The battery may be, for example, a zinc-air battery, a lithium ion battery, a lithium polymer battery, a nickel cadmium battery, or a battery using some other technology.

Figure 3:
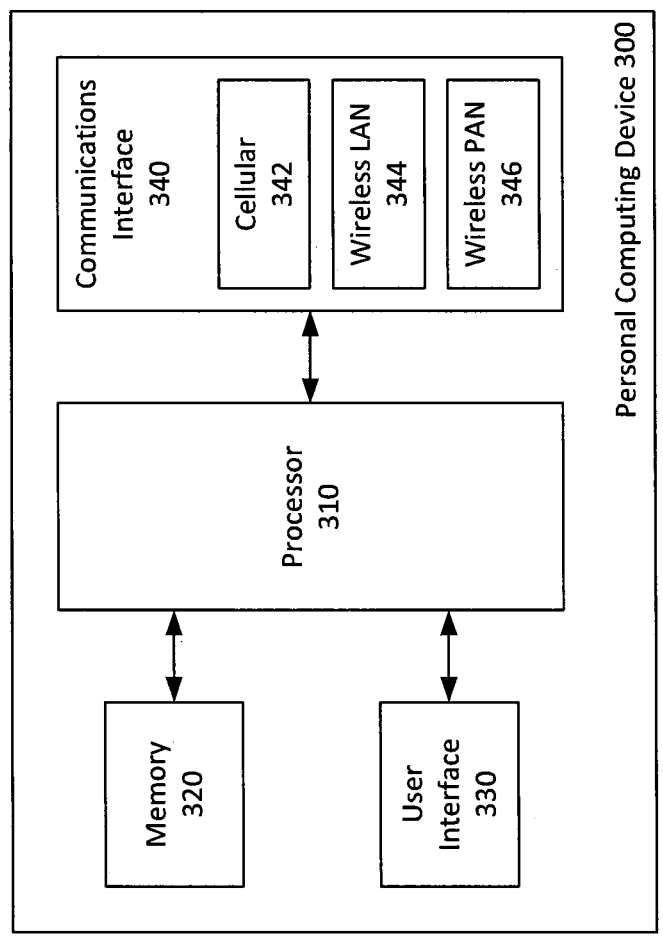
FIG. 3 is a block diagram of a personal computing device.

FIG. 3 is a block diagram of an exemplary personal computing device 300. As shown in FIG. 3, the personal computing device 300 includes a processor 310, memory 320, a user interface 330, and a communications interface 340. Some of these elements may or may not be present, depending on the implementation. Further, although these elements are shown independently of one another, each may, in some cases, be integrated into another.

The processor 310 may be or include one or more microprocessors, microcontrollers, digital signal processors, application specific integrated circuits (ASICs), or a system-on-a-chip (SOCs). The memory 320 may include a combination of volatile and/or non-volatile memory including read-only memory (ROM), static, dynamic, and/or magnetoresistive random access memory (SRAM, DRM, MRAM, respectively), and nonvolatile writable memory such as flash memory.

The communications interface 340 includes at least one interface for wireless communications with external devices. The communications interface 340 may include one or more of a cellular telephone network interface 342, a wireless Local Area Network (LAN) interface 344, and/or a wireless PAN interface 336. The cellular telephone network interface 342 may use one or more of the known 2G, 3G, and 4G cellular data protocols. The wireless LAN interface 344 may use the WiFi® wireless communications protocol or another wireless local area network protocol. The wireless PAN interface 346 may use a limited-range wireless communications protocol such as Bluetooth®, Wi-Fi®, ZigBee®, or some other wireless personal area network protocol. When the personal computing device is deployed as part of an active acoustic filter system, such as the active acoustic filter system 140, the wireless PAN interface 346 may be used to communicate with one or more active acoustic filter device 110. The cellular telephone network interface 342 and/or the wireless LAN interface 344 may be used to communicate with the cloud 130.

The communications interface 340 may include radio-frequency circuits, analog circuits, digital circuits, one or more antennas, and other hardware, firmware, and software necessary for communicating with external devices. The communications interface 340 may include one or more processors to perform functions such as coding/decoding, compression/decompression, and encryption/decryption as necessary for communicating with external devices using selected communications protocols. The communications interface 340 may rely on the processor 310 to perform some or all of these function in whole or in part.

The memory 320 may store software programs and routines for execution by the processor. These stored software programs may include an operating system such as the Apple® or Android® operating systems. The operating system may include functions to support the communications interface 340, such as protocol stacks, coding/decoding, compression/decompression, and encryption/decryption. The stored software programs may include an application or "app" to cause the personal computing device to perform portions of the processes and functions described herein.

The user interface 330 may include a display and one or more input devices including a touch screen.

Figure 4:
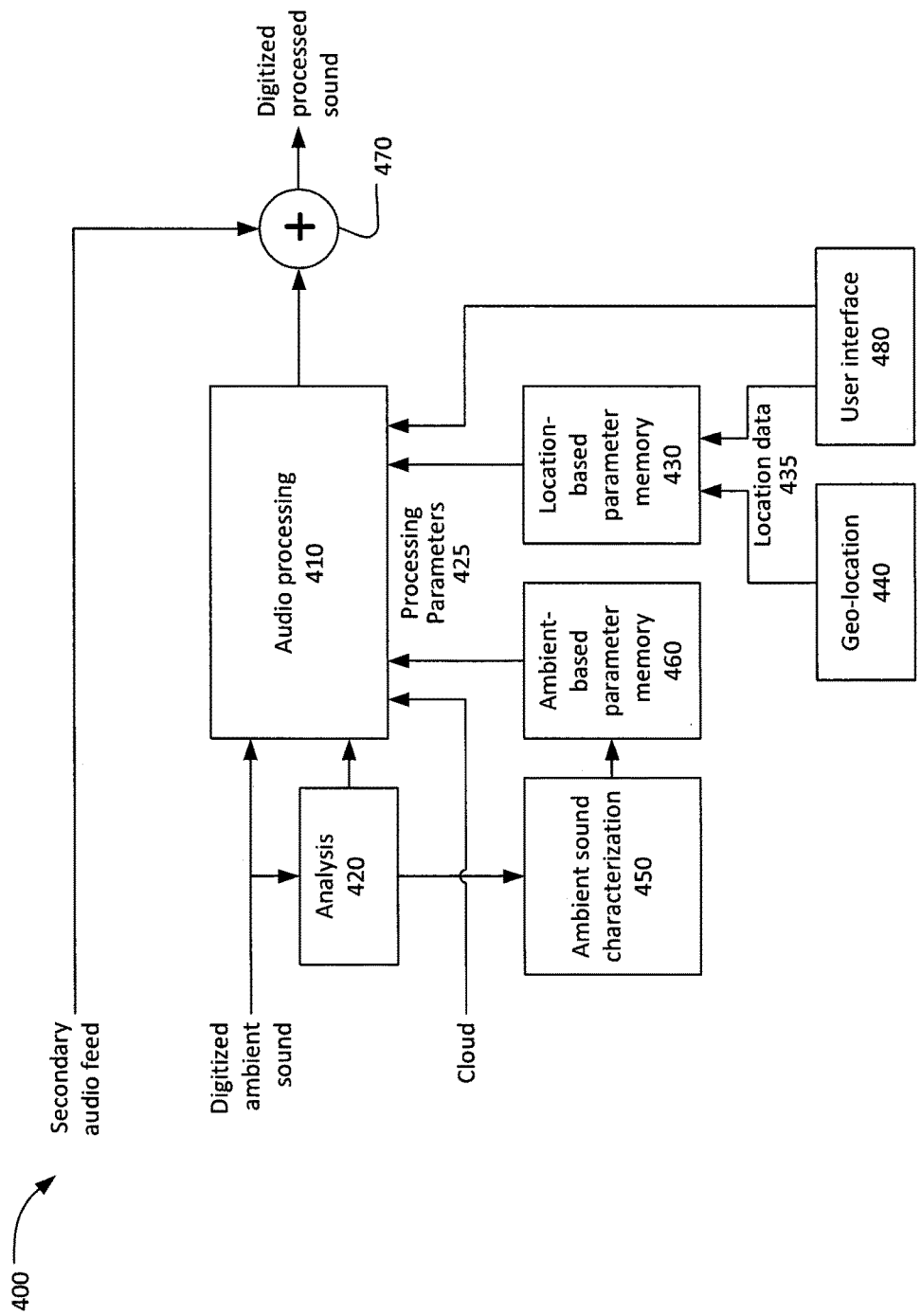
FIG. 4 is a functional block diagram of a portion of an active acoustic filter system.

FIG. 4 shows a functional block diagram of a portion of an exemplary active acoustic filter system 400, which may be the active acoustic filter system 140. Digitized ambient sound may be received, for example, from an A/D converter such as the A/D converter 220. The digitized ambient sound is processed by an audio processing function 410 implemented by a processor such as the processor 230. The processor performing the audio processing function may include one or more processor devices such as a microcontroller, a microprocessor, and/or a digital signal processor. The audio processing function 410 may include filtering, equalization, compression, limiting, and other processes. Filtering may include high-pass, low-pass, band-pass, and band-reject filtering. Equalization may include dividing the ambient sound into a plurality of frequency bands and subjecting each of the bands to a respective attenuation or gain. Equalization may be combined with filtering, such as a narrow band-reject filter to suppress a particular objectionable component of the ambient sound. Compression may be used to alter the dynamic range of the ambient sound such that louder sounds are attenuated more than softer sounds. Compression may be combined with filtering or with equalization such that louder frequency bands are attenuated more than softer frequency bands. Limiting may be used to attenuate louder sounds to a predetermined loudness level without attenuating softer sounds. Limiting may be combined with filtering or with equalization such that louder frequency bands are attenuated to a defined level while softer frequency bands are not attenuated or attenuated by a smaller amount. Techniques for implementing filters, compressors, and limiters are known to those of skill in the art of digital signal processing.

The audio processing function 410 may also include adding echo or reverberation to the ambient sound and/or detecting and cancelling an echo in the ambient sound. The audio processing function 410 may further include noise reduction processing. Techniques to add or suppress echo, to add reverberation, and to reduce noise are known to those of skill in the art of digital signal processing. The audio processing function 410 may include music effects such as chorus, pitch shifting, flanging, and/or "vinyl" emulation (adding scratches and pops to emulation vinyl records). Techniques to add these music effects are known to those of skill in the art of digital signal processing.

The audio processing function 410 may be performed in accordance with processing parameters 425. The processing parameters 425 may define the type and degree of one or more processes to be performed on the digitized ambient sound. For example, the processing parameters 425 may define filtering by a low pass filter with a particular cut-off frequency (the frequency at which the filter start to attenuate) and slope (the rate of change of attenuation with frequency) and/or compression using a particular function (e.g. logarithmic). For further example, the processing parameters 425 may define the plurality of frequency bands for equalization and provide a respective attenuation or gain for each frequency band. In yet another example, the processing parameters 425 may define a delay time and relative amplitude of an echo to be added to the digitized ambient sound. The number and format of the processing parameters 425 may vary depending on the type of processing to be performed.

The audio processing function 410 may be defined, in part, based on analysis of the ambient sound by an analysis function 420, which may be implemented by the same processor, or a different processor, as the audio processing function 410. The analysis function 420 may analyze the digitized ambient sound to determine, for example, an overall (i.e. across the entire audible frequency spectrum) loudness level or the loudness level within particular frequency bands. For further example, the analysis function 420 may transform the digitized ambient sound and/or the digitized sound output from the processing function 420 into the frequency domain using, for example, a windowed Fourier transform. The transformed sound may then be analyzed to determine the distribution of the ambient sound within the audible frequency spectrum and/or to detect the presence of dominant sounds at particular frequencies. The analysis function 420 may perform other analysis to determine other characteristics of the digitized ambient sound.

All or a portion of the processing parameters 425 for the audio processing function 410 may define processes dependent on the analysis of the ambient sound. For example, a first processing parameter may require that the overall loudness of the processed sound output from the active acoustic filter system 400 be less than a predetermined value. The analysis function 420 may determine the overall loudness of the ambient sound and the audio processing function 410 may than provide an appropriate amount of overall attenuation. For a specific example, if the overall loudness of the ambient sound is 100 phon and the processing parameter requires the output sound to be no greater than 60 phon, the audio processing function 410 may cause an overall perceptual attenuation of 40 dB. However, if the overall loudness of the ambient sound is only 40 phon, the audio processing function 410 may provide no overall attenuation. For another example, a user in a dance club may want bass frequencies (the lowest frequency portion of the audible spectrum) to be louder than any other portion of the audible frequency spectrum. In another situation, for example on an airplane, the same user may want bass frequencies to be suppressed relative to the mid-range frequencies of human speech. For further example, in the situation where the analysis function 420 detects a dominant narrow-band sound (e.g. a microphone feed-back squeal), the audio processing function 410 may provide a narrow-band band-reject filter at the corresponding frequency. In all of these examples, the audio processing function 410 may need to adapt to the characteristics of the ambient sound as determined by the analysis function 420.

The processing parameters 425 that define the processes performed in the audio processing function 410 may be received or retrieved from several sources. The processing parameters 425 may be received from a user of the active acoustic filter system 400. The user may manually enter processing parameters via a user interface 480, which may be the user interface of a personal computing device such as the personal computing device 120. Alternatively, a microphone accessible to the audio processing function 410 (such as mic 210) or a microphone in portable computing device 300 (not shown) may provide input that is used in conjunction with the audio processing function 410 and other processing parameters 425 to adjust the active acoustic filter system 400.

The processing parameters 425 may be received from a device or devices available via a computer network or otherwise available within the cloud. For example, a website accessible via the cloud may list recommended sets of processing parameters for different venues, bands, sporting events, and the like. These processing parameters 425 may be provided by an owner or operator of a venue or by an artist performing at the venue. A social media application may survey users of active acoustic filters at a particular venue or event to develop a crowd-consensus set of processing parameters for that venue or event.

The processing parameters 425 may be location-based, which is to say the processing parameters may be associated with a current location of the active acoustic filter system 400. The current location may be a specific location (e.g. "user's living room", "user's office", "Fenway Park", "Chicago O'Hare Airport", etc.) or a generic location (e.g. "sporting event", "dance club", "concert", "airplane", etc.). A location-based parameter memory 430 may store one or more sets of location-based processing parameters in association with data defining respective locations. The appropriate processing parameters may be retrieved from location-based parameter memory 430 based on location data 435 identifying the current location of the active acoustic filter system 400. The location data 435 may be provided by a geo-location function 440. The geo-location function may use GPS, cell tower signal strength, or some other technique for identifying the current location. The location data 435 may be provided by the user via the user interface 480. For example, the user may select a location from a list of locations for which processing parameters are stored in the location-based parameter memory 430. The location data 435, particularly for a generic location, may be retrieved from a cloud external to the active acoustic filter system 400. The location data 435 may obtained by some other technique.

The one or more sets of location-based processing parameters may have been stored in the location-based parameter memory 430 during prior visits to the corresponding locations. For example, the user of the active acoustic filter system 400 may manually set processing parameters for their home and save the processing parameters in the location-based parameter memory 430 in association with the location "home". Similarly, the user may set and save processing parameters for other locations (e.g. "work", "concert", "airplane", etc.). Upon returning to these locations, the corresponding processing parameters may be automatically retrieved from the location-based parameter memory 430.

The processing parameters 425 may be ambient-based, which is to say the processing parameters may be associated with particular characteristics of the ambient sound. The active acoustic filter system 400 may "listen" to the ambient sound and learn what filter parameters the user sets in the presence of various ambient sound characteristics. Once the user's listening preferences have been learned, the active acoustic filter may select or suggest processing parameters 425 appropriate for the characteristics of the current ambient sound.

For example, an ambient-based parameter memory 460 may store one or more sound "profiles" with respective sets of ambient-based processing parameters previously defined by the user for use with that ambient sound profile. Each stored sound profile may include characteristics such as, for example, an overall loudness level, the normalized or absolute loudness of predetermined frequency bands, the spectral envelop shape, spectrographic features such as rising or falling pitch, the presence and normalized or absolute loudness of dominant narrow-band sounds, the presence or absence of odd and/or even harmonics, the presence and normalized or absolute loudness of noise, low frequency periodicity (e.g. the "beat" when the ambient sound includes music), and other characteristics. An ambient sound characterization function 450, which may work in conjunction with or in parallel to the analysis function 420, may develop a profile of the current ambient sound. The profile determined by the ambient sound characterization function 450 may be used to retrieve appropriate ambient-based processing parameters from the ambient-based processing parameter memory 460.

The one or more sets of ambient-based processing parameters may have been stored in the ambient-based parameter memory 460 during prior exposure to ambient sound having particular profiles. For example, the user of the active acoustic filter system 400 may manually set processing parameters 425 during a visit to a dance club. These processing parameters may be saved in the ambient-based parameter memory 430 in association with the profile of the ambient sound in the dance club. The processing parameters 425 may be saved in the ambient-based parameter memory 430 in response to a user action, or may be automatically "learned" by the active acoustic filter system 400. Upon returning to the same or a different dance club, the appropriate ambient-based processing parameters may be automatically retrieved from the ambient-based parameter memory 460.

While FIG. 4 depicts the ambient-based parameter memory 460 and the location-based parameter memory 430 separately, these may be a common memory that associates each stored set of processing parameters with a location, with an ambient sound profile, or both. Thus, one or both of ambient-based parameters and location-based parameters may be taken into account when selecting or suggesting processing parameters 425 for a active acoustic filter system 400.

Optionally, an adder 470 may add a secondary audio feed to the output from the audio processing function 410 to produce the digitized processed sound. The secondary audio feed may be received by the active acoustic filter system 400 from an external source via a wireless communications link. For example, a user at a sporting event may receive a secondary audio feed of a sportscaster describing the event, which would then be superimposed on the processed ambient sound of the event itself.

The depiction in FIG. 4 of the active acoustic filter system 400 as a set of functional blocks or elements does not imply any corresponding physical separation or demarcation. All or portions of one or more functional elements may be located within a common circuit device or module. Any of the functional elements may be divided between two or more circuit devices or modules. For example, all or portions of the audio processing function 410, the analysis function 420, and the adder 470 may be implemented within an active acoustic filter packaged within an earbud or other housing configured to interface with a user's ear. The ambient sound characterization function 450, the ambient-based parameter memory 460 and the location-based parameter memory 430 may be distributed between the active acoustic filter and a personal computing device coupled to the active acoustic filter by a wireless communications link.

Description of Processes

Figure 5:
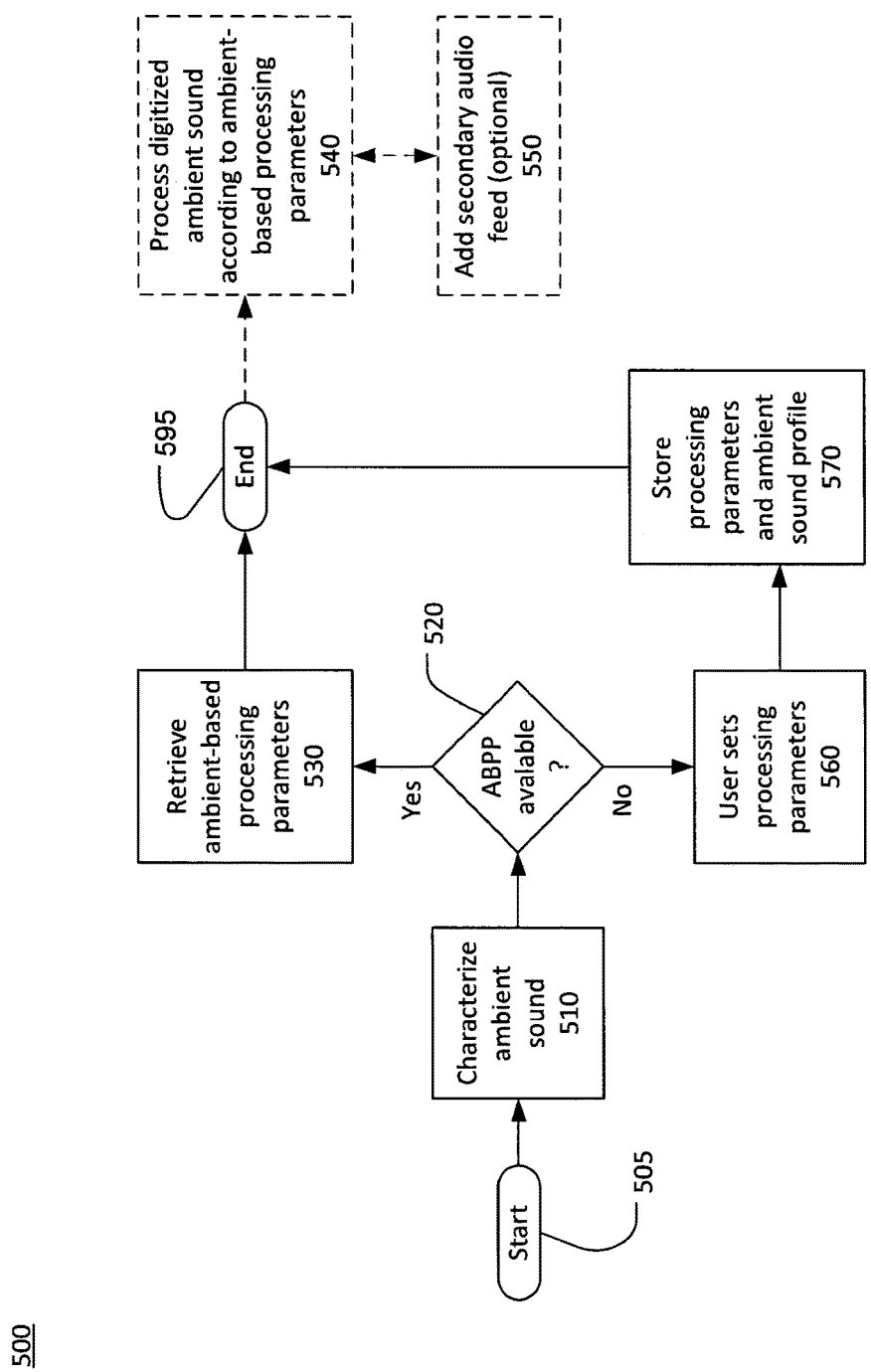
FIG. 5 is a flow chart of a method for setting processing parameters for an active acoustic filter.

Referring now to FIG. 5, a process for setting processing parameters for an active acoustic filter, such as the active acoustic filter 200, begins at 505 and ends at 595. The process 500 may be initiated by a user, or may be initiated automatically in recognition of a significant change in the characteristics of the ambient sound. At 510, the ambient sound may be characterized to determine an ambient sound profile. The ambient sound profile may include characteristics such as overall loudness, normalized or absolute loudness of predetermined frequency bands, the presence of dominant narrow-band sounds or random noise, and/or other characteristics.

At 520, a determination may be made whether or not ambient-based processing parameters (ABPP) are available for ambient sound having a profile that is the same or reasonably similar to the profile determined at 510. "Ambient-based" processing parameters are sets of processing parameters tailored for specific ambient sound characteristics. For example, a memory may store sound profiles for one or more environments in association with respective sets of ambient-based processing parameters. At 520, the profile determined at 510 may be compared with the sound profiles stored in the memory to determine if the memory holds a stored sound profile that "matches" (e.g. is the same as, or a reasonably similar to) the ambient sound profile determined at 510.

When a determination is made at 520 that the memory holds a stored sound profile that "matches" (e.g. is the same as, or a reasonably similar to) the ambient sound profile determined at 510 ("yes" at 520), the appropriate ambient-based processing parameters associated with the matching stored sound profile may be retrieved at 530.

After retrieving ambient-based processing parameters for the current ambient sound at 530, the process 500 may end at 595. Note that, while the process 500 for setting processing parameters has ended, the use of the ambient-based processing parameters may continue. Specifically, the ambient-based processing parameters may be used to process ambient sound at 540, including adding a secondary audio feed if available at 560.

When a determination is made at 520 that the memory does not hold a stored sound profile that "matches" (e.g. is the same as, or a reasonably similar to) the ambient sound profile determined at 510 ("No" at 520), the user may set processing parameters for the active acoustic filter at 560. For example, a graphical user interface may be provided on a display of the user's personal computing device to allow the user to enter processing parameters. Alternatively or additionally, the graphical user interface may allow the user to select previously stored or predetermined set of processing parameters from a list or menu. A further graphical user interface may be provided to allow the user to edit a selected set of processing parameters.

At 570, the processing parameters set at 560 may be stored as ambient-based processing parameters in association with the ambient sound profile determined at 510. Storing the ambient-based processing parameters and associated sound profile at 570 may be automatic, or may be optional and initiated by a user action. The ambient-based processing parameters may be stored within the active acoustic filter, within the user's personal computing device, and/or on the cloud.

After ambient-based processing parameters for the current ambient sound characteristics have been set at 560 and optionally stored at 570, the process 500 may end at 595. The use of the ambient-based processing parameters may continue at 540 and 550 as previously described.

Figure 6:
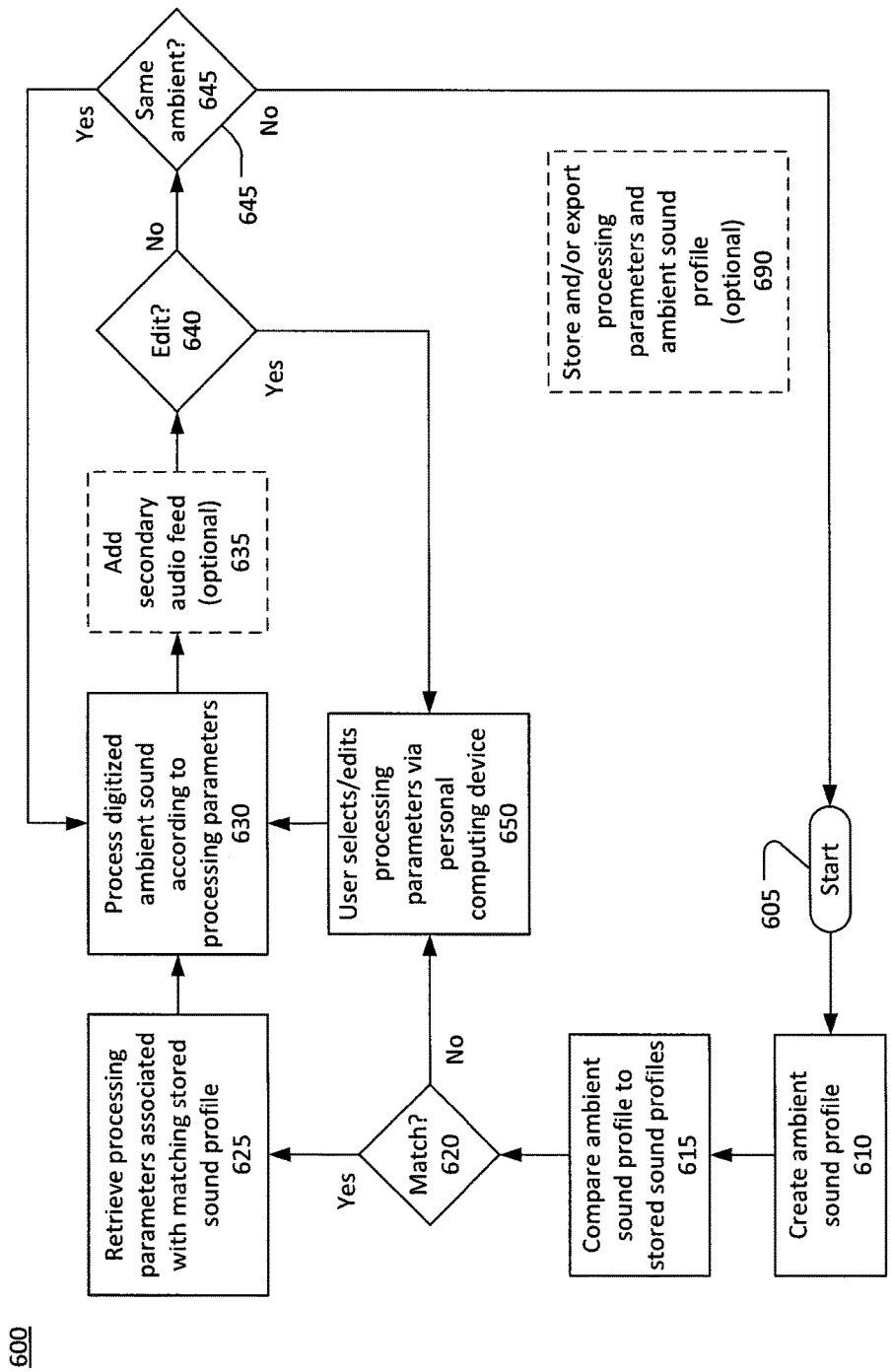
FIG. 6 is a flow chart of a method for processing ambient sound.

Referring now to FIG. 6, a process 600 for processing ambient sound using an active acoustic filter system, such as the active acoustic filter system 140, begins at 605 and may run continuously until stopped by a user action (not shown). The process 600 may be initiated by a user, or may be initiated automatically at regular intervals or in recognition of a significant change in the characteristics of the ambient sound. At 610, the ambient sound may be characterized to determine an ambient sound profile. The ambient sound profile may include characteristics such as an overall loudness level, normalized or absolute acoustic power within predetermined frequency bands, normalized or absolute power level of dominant narrow-band sounds and/or random noise, beat or onset frequency (when the ambient sound includes music), and/or other characteristics.

At 615, the ambient sound profile from 610 may be compared to one or more sound profiles stored within the action acoustic filter system 140. The stored sound profiles may be stored within an active acoustic filter, within a personal computing device, and/or within a cloud, which may be the active acoustic filter 110, the personal computing device 120, and the cloud 130 of FIG. 1, respectively. Each of the stored sound profiles may be associated with a corresponding set of ambient-based processing parameters.

At 620, a determination may be made whether or not the ambient sound profile from 610 matches one of the stored sound profiles. In this context, the term "matches" means "is the same as within predetermined limits" using one or more similarity metrics and comparison criteria.

Figure 7:
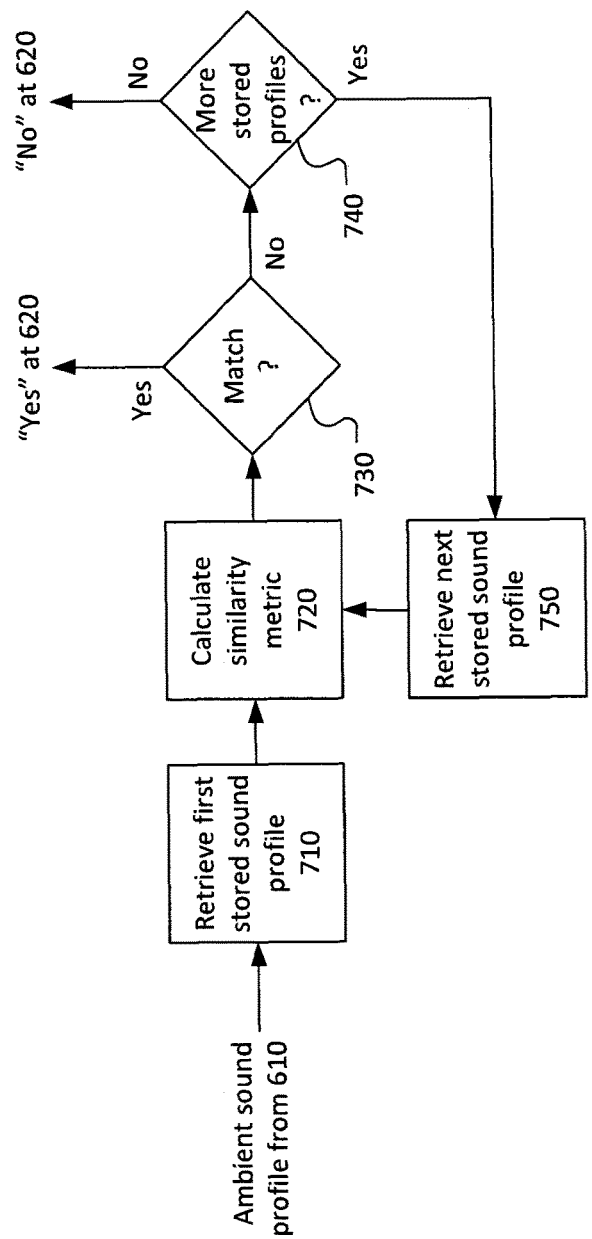
FIG. 7 is a flow chart of a method for comparing sound profiles.

An exemplary method for determining whether or not the ambient sound profile matches a stored sound profile is shown in FIG. 7. The process 700 may begin after an ambient sound profile is computed at 610 in the process 600. At 710, a first one of one or more stored sound profiles may be retrieved from memory. Each of the one or more stored sound profiles may be stored in a memory is association with a set of processing parameters. A similarity metric between the ambient sound profile and the retrieved sound profile may be calculated at 720.

For example, the ambient sound profile and each of the stored sound profiles may consist of an ordered set of n numbers (where n is a positive integer) representing various parameters of the sound as previously described (e.g. overall loudness level, normalized or absolute acoustic power within predetermined frequency bands, normalized or absolute power level of dominant narrow-band sounds and/or random noise, beat or onset frequency, etc.). Thus the ambient sound profile and each stored sound profile may be considered as vectors in an n-dimensional space. The similarity metric used for comparison of the ambient sound profile and a stored sound profile may then be the Euclidean distance between the corresponding vectors. Other similarity metrics that may be used at 720 instead of, or in addition to, Euclidean distance include a radial basis function between the vectors, spectral or spectrographic comparisons, and other similarity metrics known to those of skill in the art.

At 730, a determination may be made if the similarity metric calculated at 720 indicates that the ambient sound profile and the stored sound profile "match" according to a predetermined criteria. For example, assuming a similarity metric such as Euclidean distance where a lower value indicates greater similarity, the determination at 730 may be whether or not the similarity metric is less than or equal to a predetermined threshold. For a similarity metric where a high value indicates greater similarity, the determination at 730 may be whether or not the similarity metric is greater than or equal to a predetermined threshold. When the ambient sound profile and stored sound profile match ("Yes" at 730), the process 700 may return a "Yes" answer at 620 in the process 600.

When a determination is made at 730 that the ambient sound profile and the stored sound profile do not match according to the predetermined criteria ("No" at 730), a further determination may be made if additional stored sound profiles are available for comparison. When there are more stored sound profiles ("Yes" at 740), a next stored sound profile may be retrieved at 740 and the process 700 may repeat until a match is found at 730 or all of the stored sound profiles have been compared to the ambient sound profile. When all of the stored sound profiles have been compared to the ambient sound profile without finding a match ("No" at 740), the process 700 may return a "No" answer at 620 in the process 600.

Referring back to FIG. 6, when the ambient sound profile from 610 matches one of the stored sound profiles ("yes" at 620), the ambient-based processing parameters associated with the matching stored sound profile may be retrieved at 625 and used to process the ambient sound at 630. Optionally, a secondary audio feed may be added to the processed ambient sound at 635.

At 640, a determination may be made whether or not the current processing parameters (i.e. the processing parameters currently in use) will be edited. Editing may be requested by a user via a user interface on a personal computing device. When editing is requested ("yes" at 640), the user may edit the current processing parameters or enter new processing parameters at 650. Editing may be done, for example, via a graphical user interface on the personal computing device. The edited processing parameters may then be used to process the ambient sound at 630.

When editing is not requested ("no" at 640), a determination may be made at 645 whether or not the ambient sound is still the same as, or reasonably similar to, the ambient sound when the process 600 was started at 605. When the ambient sound is the same ("yes" at 645), the process 600 returns to 630. When the ambient sound has changed ("no" at 645) the process 600 may return to the start at 605. While the actions at 630, 635, 640 and 645 are shown as sequential steps for ease of discussion, these actions may be performed concurrently and continuously until a determination is made at 640 to edit the processing parameters or a determination is made at 645 to restart the process.

The determination at 645 may be solely a user decision. In this case the default decision at 645 is "Yes" (the ambient is the same) unless the user provides an input via the personal computing device to indicate the ambient has changed.

The active acoustic filter system may be enabled to make an automatic determination at 645. In this case, the active acoustic filter system may continuously or periodically create a profile of the current ambient sound and compare the current ambient sound profile to the original ambient sound profile created at 610. For example, the comparison at 645 may be made using the same similarity metric and criteria used at 615 and 620. To avoid repeated switching between sets of processing parameters, the process 600 may be restarted at 605 only if the current and original ambient sound profiles are found to be substantially different for longer than a predetermined time period. When an automatic determination at 645 is enabled, the user may have an option to manually provide an input via the personal computing device to indicate the ambient has changed.

The current processing parameters may optionally be stored in memory in association with the current ambient sound profile at 690. The current processing parameters and ambient sound profile may be stored automatically each time the user enters new processing parameters at 650. Automatic storage of new processing parameters allows the active acoustic filter system to "learn" and subsequently reuse the user's processing preferences. Alternatively or additionally, the user may enter a "store command" via the personal computing to device to cause the current processing parameters and ambient sound profile to be stored at 690. The user may have the option to enter the store command only after editing or entering processing parameters at 650. The user may have the option to enter the store command at any time during the process 600.

Figure 8:
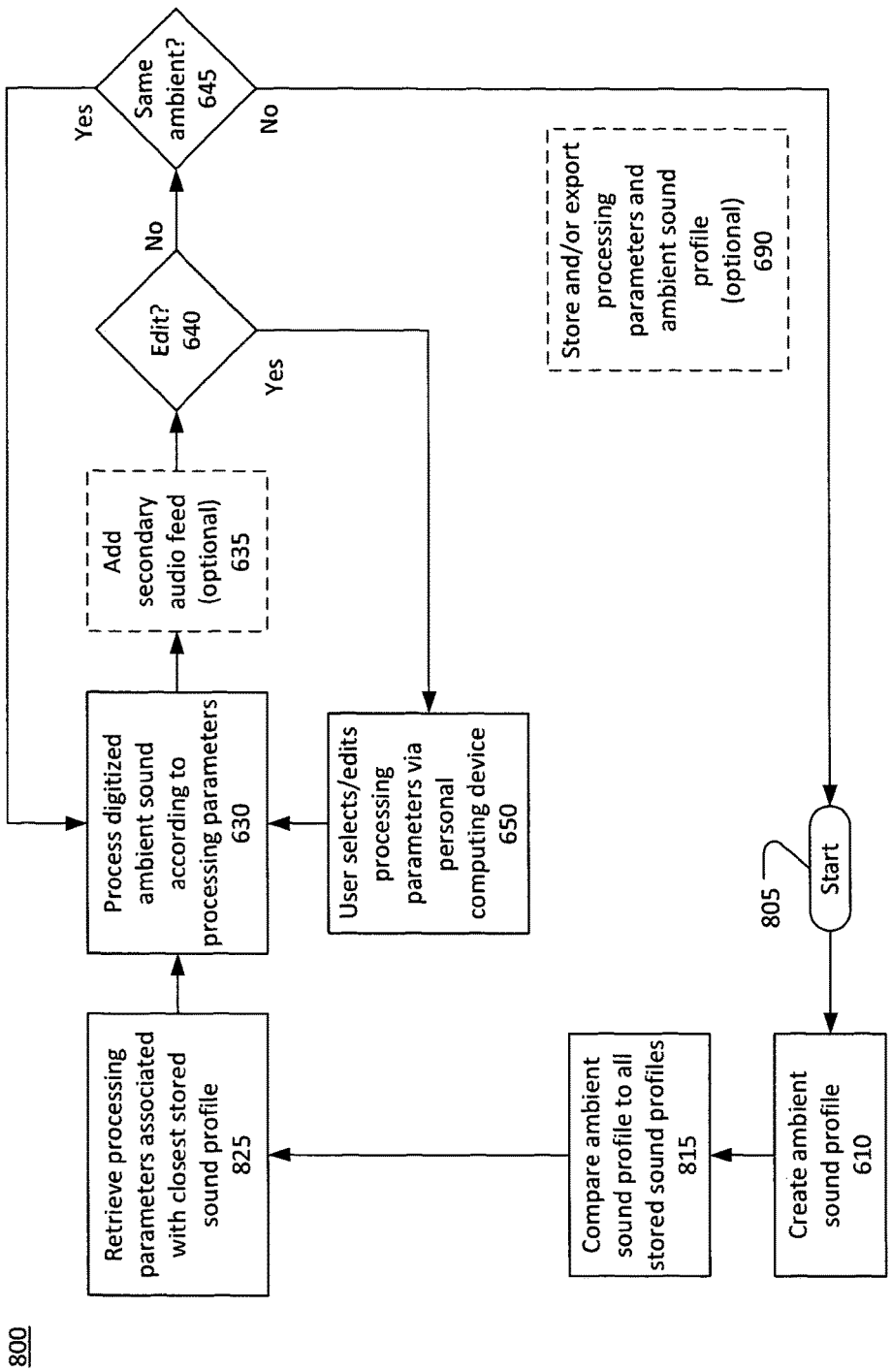
FIG. 8 is a flow chart of another method for processing ambient sound.

Referring now to FIG. 8, another process 800 for processing ambient sound using an active acoustic filter system, such as the active acoustic filter system 140, begins at 805 and may run continuously until stopped by a user action (not shown). The process 800 may be initiated by a user, or may be initiated automatically in recognition of a significant change in the characteristics of the ambient sound. Elements of the process 800 with reference designators from 610 to 690 were previously described in conjunction with FIG. 6. Descriptions of these elements will not be repeated.

At 815, an ambient sound profile created at 610 may be compared to all of one or more sound profiles stored within the active acoustic filter system. The stored sound profiles may be stored within an active acoustic filter, within a personal computing device, and/or within a cloud, which may be the active acoustic filter 110, the personal computing device 120, and the cloud 130 of FIG. 1, respectively. Each of the stored sound profiles may be associated with a corresponding set of ambient-based processing parameters. The comparisons may be performed using a similarity metric as previously described. A determination may then be made which of the one or more stored sound profiles is closest to the ambient sound profile. For example, in the case where similarity metric is Euclidean distance, the smallest Euclidean distance indicates the "closest" stored sound profile. Note that the closest stored sound profile may not necessarily "match" the ambient sound profile using any predetermined criteria.

The ambient-based processing parameters associated with the closest stored sound profile may be retrieved at 825 and used to process the ambient sound at 630. The process 800 may continue as previously described in conjunction with FIG. 6.

Figure 9:
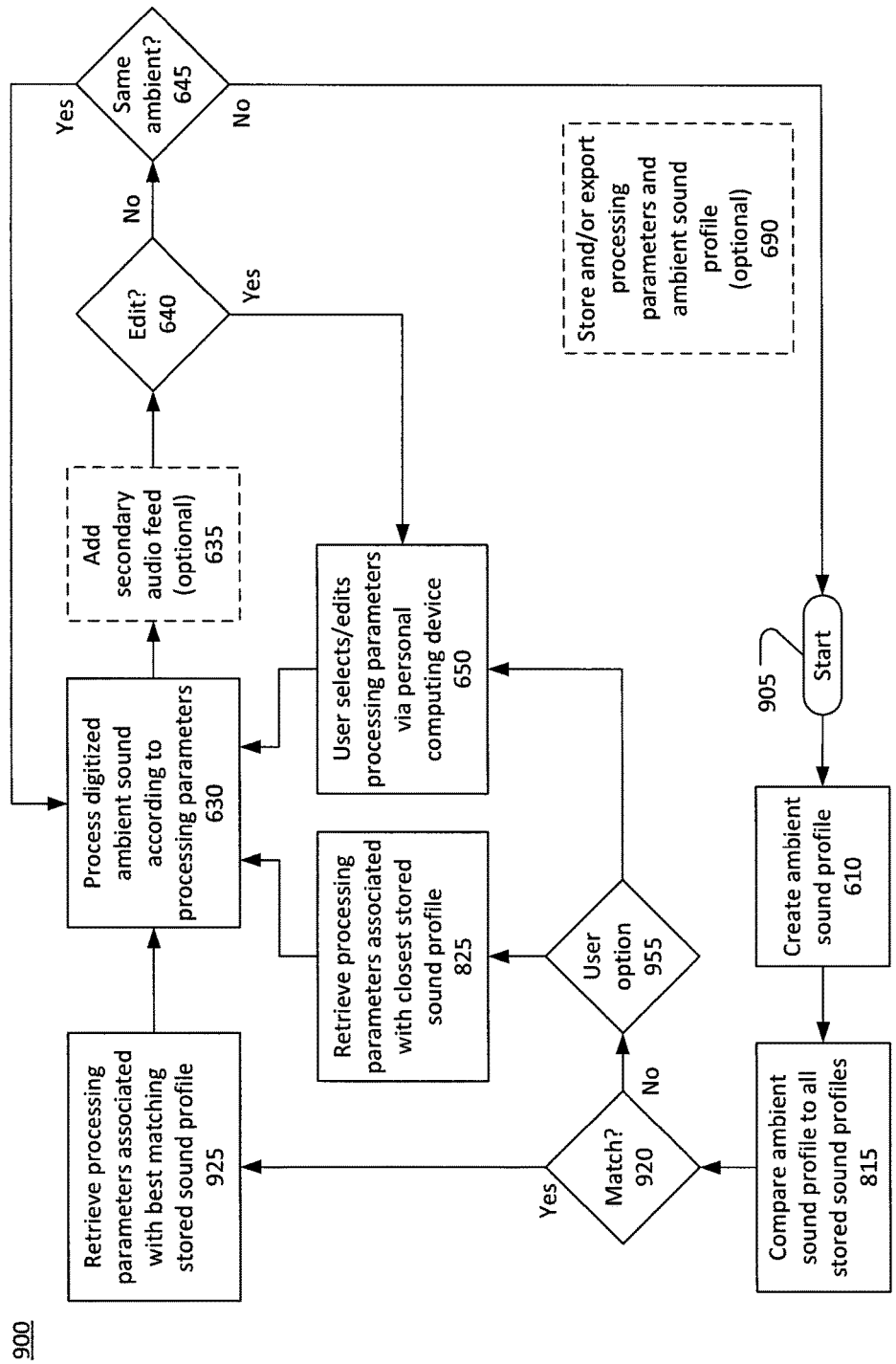
FIG. 9 is a flow chart of another method for processing ambient sound.

Referring now to FIG. 9, another process 900 for processing ambient sound using an active acoustic filter system, such as the active acoustic filter system 140, begins at 905 and runs continuously until stopped by a user action (not shown). The process 900 may be initiated by a user, or may be initiated automatically in recognition of a significant change in the characteristics of the ambient sound. Elements of the process 900 with reference designators from 610 to 690 were previously described in conjunction with FIG. 6. Elements of the process 900 with reference designators 815 and 825 were previously described in conjunction with FIG. 8. Descriptions of these elements will not be repeated.

At 815, an ambient sound profile created at 610 may be compared to all of one or more sound profiles stored within the active acoustic filter system as previously described. At 620, a determination may be made if one or more of the stored sound profiles match the ambient sound profile from 610 according to a predetermined criterion. If one or more of the stored sound profiles match the ambient sound profile ("yes" at 620), the ambient-based processing parameters associated with the best-matching stored sound profile may be retrieved at 925 and used to process ambient sound at 630. The process 900 may continue as previously described in conjunction with FIG. 6.

If none of the stored sound profiles matches the ambient sound profile ("no" at 620), the user may be provided with an option at 955 to either retrieve the processing parameters associated with the closest stored sound profile at 825 or to enter new processing parameters at 650. In either case, the retrieved or enter processing parameters are then used to process ambient sound at 630. The process 900 may continue as previously described in conjunction with FIG. 6.

Closing Comments

Throughout this description, the embodiments and examples shown should be considered as exemplars, rather than limitations on the apparatus and procedures disclosed or claimed. Although many of the examples presented herein involve specific combinations of method acts or system elements, it should be understood that those acts and those elements may be combined in other ways to accomplish the same objectives. With regard to flowcharts, additional and fewer steps may be taken, and the steps as shown may be combined or further refined to achieve the methods described herein. Acts, elements and features discussed only in connection with one embodiment are not intended to be excluded from a similar role in other embodiments.

As used herein, "plurality" means two or more. As used herein, a "set" of items may include one or more of such items. As used herein, whether in the written description or the claims, the terms "comprising", "including", "carrying", "having", "containing", "involving", and the like are to be understood to be open-ended, i.e., to mean including but not limited to. Only the transitional phrases "consisting of" and "consisting essentially of", respectively, are closed or semi-closed transitional phrases with respect to claims. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. As used herein, "and/or" means that the listed items are alternatives, but the alternatives also include any combination of the listed items.

What is claimed is:

1. An active acoustic filter system, comprising:
    a housing;
    an active acoustic filter configured to convert ambient sound into digitized ambient sound, wherein the active acoustic filter comprises a microphone, a preamplifier, an analog to digital converter, a digital to analog converter, an amplifier, and a speaker that are disposed within the housing;
    a memory storing one or more stored sound profiles and a respective set of processing parameters associated with each of the one or more stored sound profiles;
    one or more processors, at least one of the one or more processors being enclosed by the housing and configured for communication with the memory, the at least one of the one or more processors being configured to:
analyze the digitized ambient sound to create an ambient sound profile;
determine whether or not the ambient sound profile matches one of the one or more stored sound profiles; and
when the ambient sound profile matches one of the one or more stored sound profiles:
retrieve the set of processing parameters associated with the stored sound profile that matches the ambient sound profile, and
generate digitized processed sound by processing the digitized ambient sound in accordance with the set of processing parameters retrieved from the memory; and
when the ambient sound profile does not match one of the one or more stored sound profiles, generate digitized processed sound by processing the digitized ambient sound in accordance with processing parameters established by a user of the active acoustic filter, wherein the processing parameters adjust one or more decibel levels associated with frequency ranges of the digitized ambient sound, wherein the active acoustic filter is configured to convert the digitized processed sound into processed output sound.

2. The active acoustic filter system of claim 1, wherein the processor is configured to determine whether or not the ambient sound profile matches one or more of the stored sound profiles by calculating a similarity metric between the ambient sound profile and the stored sound profile.

3. The active acoustic filter system of claim 2, wherein each of the one or more stored sound profiles and the ambient sound profile is expressed as an n-dimensional vector, where n is a integer greater than one, and the similarity metric is an Euclidean distance between the respective vectors.

4. The active acoustic filter system of claim 1, wherein the housing is configured to interface with a user's ear by fitting in, on, or over the user's ear.

5. The active acoustic filter system of claim 4, wherein the housing is configured to exclude most ambient sound from reaching the user's ear canal.

6. The active acoustic filter system of claim 1, wherein the housing is an earbud housing configured to fit, at least partially, within and be supported by a user's ear.

7. The active acoustic filter system of claim 1, wherein the memory is disposed within the housing.

8. The active acoustic filter system of claim 1, further comprising a personal computing device configured for communication with the processor via a wireless communications link.

9. The active acoustic filter system of claim 1, wherein processing the digitized ambient sound includes one or more of amplification, attenuation, equalization, reverberation, and noise suppression.

10. The active acoustic filter system of claim 1, wherein each set of processing parameters includes parameters to cause the processor to perform one or more of amplification, attenuation, equalization, reverberation, and noise suppression.

11. The active acoustic filter system of claim 1, wherein the ambient sound profile comprises a plurality of n characteristics and is represented as a vector of the plurality of n characteristics, wherein each of the plurality of n characteristics is a different type of characteristic of ambient sound experienced by the active acoustic filter system.

12. The active acoustic filter system of claim 11, wherein the plurality of n characteristics include two or more of an overall loudness level, normalized acoustic power within predetermined frequency bands, absolute acoustic power within predetermined frequency bands, normalized and/or absolute power level of dominant narrow-band sounds and/or random noise, beat frequency, or onset frequency.

13. The active acoustic filter system of claim 1, wherein the processor is further configured to add a secondary audio feed to the digitized processed sound.

14. A method, comprising:
converting, by an active acoustic filter, ambient sound into digitized ambient sound, wherein the active acoustic filter comprises a microphone, a preamplifier, an analog to digital converter, a digital to analog converter, an amplifier, and a speaker that are disposed within a housing;
storing, in a memory, one or more stored sound profiles and a respective set of processing parameters associated with each of the one or more stored sound profiles;
analyzing the digitized ambient sound to create an ambient sound profile;
determining whether or not the ambient sound profile matches one of the one or more stored sound profiles;
generating digitized processed sound by processing the digitized ambient sound in accordance with whether the ambient sound profile matches one of the one or more stored sound profiles; and
converting the digitized processed sound into processed output sound wherein:
the converting, analyzing, determining and generating are performed by a processor disposed within the housing;
when the ambient sound profile does not match one of the one or more stored sound profiles, the method further comprises generating, by the processor, the digitized processed sound by processing the digitized ambient sound in accordance with processing parameters established by a user of the active acoustic filter; and
the processing parameters adjust one or more decibel levels associated with frequency ranges of the digitized ambient sound.

15. The method of claim 14, wherein determining whether or not the ambient sound profile matches one of the one or more stored sound profiles comprises calculating a similarity metric between the ambient sound profile and the stored sound profile.

16. The method of claim 15, wherein
each of the one or more stored sound profiles and the ambient sound profiles is expressed as an n-dimensional vector, where n is a integer greater than one, and
the similarity metric is an Euclidean distance between the respective vectors.

17. The method of claim 14, wherein the housing is configured to fit, at least partially, within and be supported by a user's ear.

18. The method of claim 14, wherein the memory is disposed within the housing.

19. The method of claim 14, wherein, when the ambient sound profile matches one of the one or more stored sound profiles, the method further comprises:
retrieving the set of processing parameters associated with the stored sound profile that matches the ambient sound profile, and generating, by the processor, digitized processed sound by processing the digitized ambient sound in accordance with the set of processing parameters retrieved from the memory.

20. A computer program product, the computer program product being embodied in a tangible non-transitory computer readable storage medium and comprising instructions which, when executed by a processor, cause the processor to perform the steps of:

converting ambient sound into digitized ambient sound, wherein the ambient sound is converted into digitized ambient sound by an active acoustic filter that comprises a microphone, a preamplifier, an analog to digital converter, a digital to analog converter, an amplifier, and a speaker that are disposed within a housing;

storing, in a memory, one or more stored sound profiles and a respective set of processing parameters associated with each of the one or more stored sound profiles;

analyzing the digitized ambient sound to create an ambient sound profile;

determining whether or not the ambient sound profile matches one of the one or more stored sound profiles;

when the ambient sound profile matches one of the one or more stored sound profiles:

retrieving the set of processing parameters associated with the stored sound profile that matches the ambient sound profile, and generating digitized processed sound by processing the digitized ambient sound in accordance with the set of processing parameters retrieved from the memory; and when the ambient sound profile does not match one of the one or more stored sound profiles:

generating the digitized processed sound by processing the digitized ambient sound in accordance with processing parameters established by a user of the active acoustic filter, wherein the processing parameters adjust one or more decibel levels associated with frequency ranges of the digitized ambient sound; and convert the digitized processed sound into processed output sound, wherein the converting, analyzing, determining and generating are performed by a processor disposed within the housing.

* * * * *